(12) United States Patent
Weiguny et al.

(10) Patent No.: US 7,060,649 B2
(45) Date of Patent: Jun. 13, 2006

(54) METHOD FOR THE PRODUCTION OF A CATALYST CONTAINING VANADIUM, PHOSPHORUS, AND OXYGEN

(75) Inventors: Jens Weiguny, Shanghai (CN); Sebastian Storck, Mannheim (DE); Mark Duda, Ludwigshafen (DE); Cornelia Dobner, Frankenthal (DE); Raimund Felder, Neustadt (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 6 days.

(21) Appl. No.: 10/507,601

(22) PCT Filed: Mar. 12, 2003

(86) PCT No.: PCT/EP03/02502

§ 371 (c)(1),
(2), (4) Date: Sep. 14, 2004

(87) PCT Pub. No.: WO03/078310

PCT Pub. Date: Sep. 25, 2003

(65) Prior Publication Data

US 2005/0153834 A1 Jul. 14, 2005

(30) Foreign Application Priority Data

Mar. 15, 2002 (DE) .................... 102 11 446

(51) Int. Cl.
| | |
|---|---|
| B01J 27/198 | (2006.01) |
| B30B 15/30 | (2006.01) |
| F16P 3/00 | (2006.01) |
| F16P 3/18 | (2006.01) |
| F16P 3/05 | (2006.01) |

(52) U.S. Cl. .................... 502/209; 100/215; 100/342; 100/344; 100/345

(58) Field of Classification Search .................. 502/209; 100/215, 342, 344, 345
See application file for complete search history.

(56) References Cited

U.S. PATENT DOCUMENTS

| 4,567,158 A | | 1/1986 | Wrobleski et al. .......... 502/209 |
|---|---|---|---|
| 4,699,985 A | * | 10/1987 | Bither, Jr. .................... 549/260 |
| 4,849,539 A | * | 7/1989 | Bergna ........................ 558/323 |
| 4,996,179 A | | 2/1991 | Haddad et al. ............. 502/209 |

(Continued)

FOREIGN PATENT DOCUMENTS

WO 02/24620 3/1992

(Continued)

Primary Examiner—J. A. Lorengo
Assistant Examiner—Patricia L. Hailey
(74) Attorney, Agent, or Firm—Jason D. Voight

(57) ABSTRACT

Disclosed is a method for producing a catalyst containing vanadium, phosphorus, and oxygen, which is used for oxidizing the gas phase of a hydrocarbon having at least four carbon atoms to maleic anhydride. According to the inventive method, a corresponding catalyst precursor which contains vanadium, phosphorus, and oxygen and is provided with particles having an average diameter of at least 2 mm is converted into a catalytically active form by means of calcination, and a flow of the catalyst precursor is transported on a conveyor belt across at least one calcination area over a distance $1_n$ at an essentially steady speed in order to be calcinated. The variation over time of the gas temperature in relation to the set point value amounts to $\leq 5°$ C. at each position in the area of the flow of the catalyst precursor, which lies within the second half $1_n/2$ of the calcination area, while the local difference in the gas temperature between any positions in the area of the flow of the catalyst precursor, which is located within the second half $1_n/2$ of the calcination area, amounts to $\leq 5°$ C.

15 Claims, 2 Drawing Sheets

U.S. PATENT DOCUMENTS

Figure 1:
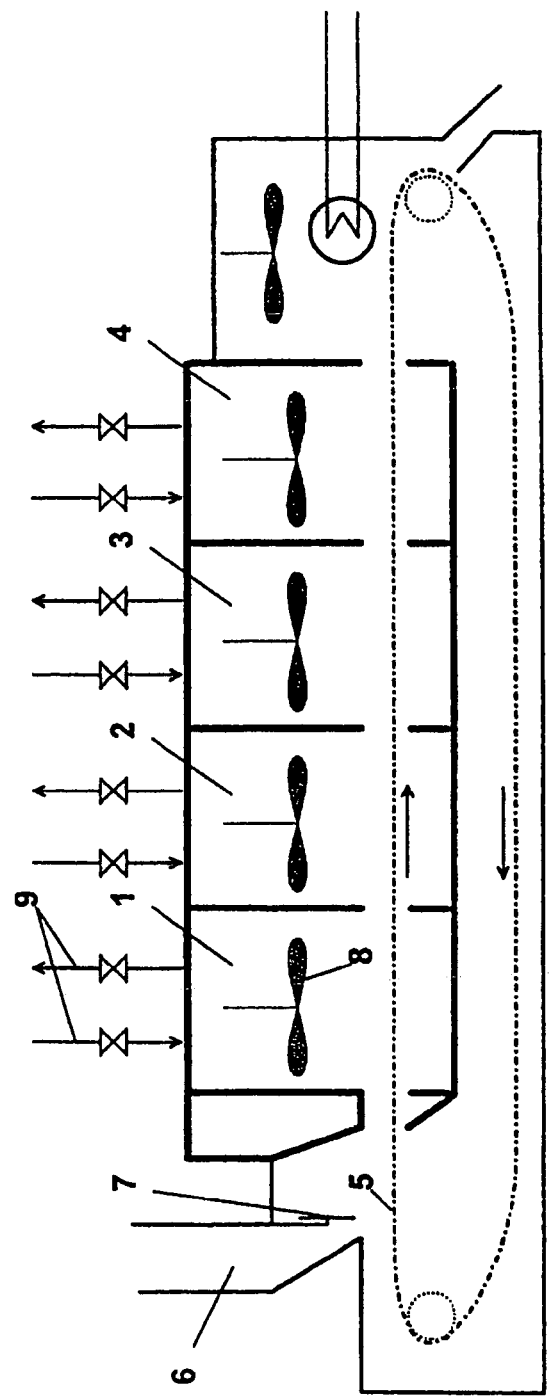

| | | | |
|---|---|---|---|
| 5,004,718 A * | 4/1991 | Ishida et al. | 502/217 |
| 5,137,860 A | 8/1992 | Ebner et al. | 502/209 |
| 5,275,996 A | 1/1994 | Andrews et al. | 502/209 |
| 5,506,187 A | 4/1996 | Haddad et al. | 502/209 |
| 5,530,144 A | 6/1996 | Tsurita et al. | 549/259 |
| 5,641,722 A | 6/1997 | Mitchell et al. | 502/209 |
| 5,773,382 A | 6/1998 | Mitchell et al. | 502/209 |
| 6,740,779 B1 * | 5/2004 | Tenten et al. | 562/598 |
| 6,881,702 B1 * | 4/2005 | Arnold et al. | 502/311 |

FOREIGN PATENT DOCUMENTS

| | | |
|---|---|---|
| WO | 97/12674 | 4/1997 |

* cited by examiner

METHOD FOR THE PRODUCTION OF A CATALYST CONTAINING VANADIUM, PHOSPHORUS, AND OXYGEN

The present invention relates to a process for preparing a vanadium, phosphorus, and oxygen catalyst suitable for heterogeneously catalyzed gas-phase oxidation of a hydrocarbon having at least four carbon atoms to maleic anhydrides, in which a corresponding vanadium, phosphorus, and oxygen catalyst precursor containing particles having an averaged diameter of at least 2 mm is converted into a catalytically active form by calcining.

The present invention further relates to a process for preparing maeic anhydride by heterogeneously catalyzed gas-phase oxidation of a hydrocarbon having at least four carbon atoms using a catalyst prepared by the first process of the invention.

Maleic anhydride is an important intermediate in the synthesis of γ-butyrolactone, tetrahydrofuran, and 1,4-butanediol, which in turn are used as solvents or else processed further to give, for example, polymers, such as polytetrahydrofuran or polyvinylpyrrolidone.

The preparation of maleic anhydride by oxidizing hydrocarbons such as n-butane, n-butenes or benzene over appropriate catalysts is well established. It is generally performed using vanadium-phosphorus-oxygen catalysts (known as VPO catalysts) (see Ullmann's Encyclopedia of Industrial Chemistry, 6$^{th}$ edition, 2000 electronic release, Chapter "MALEIC AND FUMARIC ACIDS, Maleic Anhydride—Production").

Since the oxidation of said hydrocarbons to maleic anhydride is highly exothermic, the reaction is generally conducted in a salt-bath-cooled, fixed-bed shell-and-tube reactor. Depending on the size of the plant, the catalyst-filled tubes of said reactor number from a few thousand to several tens of thousands. The heat of reaction formed is transferred through the walls of the catalyst-filled tubes to the surrounding salt bath, generally a eutectic mixture of potassium nitrate and sodium nitrate, and is dissipated. Despite this salt bath cooling, the temperature which becomes established over the length and cross section of the catalyst-filled tubes is not uniform. Overheated regions referred to as hot spots are formed. Accordingly, the hydrocarbon concentration of the reaction mixture is at its highest in the vicinity of the entry point of the catalyst-filled tubes and at its lowest in the vicinity of the exit point, leading to the formation of said hot spots in the vicinity of the entry point.

The formation of hot spots in the catalyst-filled tubes is disadvantageous for a variety of reasons. Within the hot spots there is excessive oxidation beyond the desired oxidation state. Furthermore, the excessive thermal load affects the performance and lifetime of the catalyst. Since the increase in temperature is accompanied by an increase in reaction rate and hence by the production of even greater quantities of heat, the formation of hot spots may lead ultimately to uncontrolled progress of the reaction, possibly culminating in an explosive reaction runaway.

Although setting a low reaction temperature would act to counter the abovementioned disadvantages of the hot spots, it would also mean an uneconomically low conversion and hence an uneconomically low yield of target product.

On economic and safety grounds, therefore, the shell-and-tube reactor is operated so that the reaction temperature is as high as possible in order to ensure an economically attractive yield but without the hot spots which develop in the individual tubes leading to an uncontrolled reaction. In practice, the temperatures which establish themselves within the individual tubes are not exactly the same. Ultimately, it is the reaction temperature of the hottest tube which is critical for the operation of the shell-and-tube reactor as a whole. The greater the temperature spread, the lower the average reaction temperature must be set, for safety reasons. A low spread is therefore desirable. Consequently, when filling the tubes with catalyst, care is taken to ensure that the same amount of catalyst and/or the same catalyst mixture is present in every tube. It is also customary, after filling the tubes with catalyst, to conduct what is known as a pressure balancing operation and to set the same flow resistance in all the tubes by adding further inert material. Taking this measure ensures that, in operation, the same volume of gas flows through all of the tubes.

In accordance with the invention it was recognized that even the measures described above still leave considerable differences in the temperatures established in the individual catalyst-filled tubes. It was further recognized in accordance with the invention that these differences were largely attributable to the catalyst used when filling the tubes. In effect, where the entirety of the catalyst exhibits particles of differing activity, some of the catalyst is inevitably operated at a temperature which differs to a greater or lesser extent from the optimum temperature range of the respective catalyst particles. Such operation is associated with detractions in terms of yield and of catalyst lifetime.

The vanadium-phosphorus-oxygen catalysts generally employed are normally prepared as follows:

(1) synthesis of a vanadyl phosphate hemihydrate (VOHPO$_4$·½H$_2$O) precursor from a pentavalent vanadium compound (e.g., V$_2$O$_5$), a pentavalent or trivalent phosphorus compound (e.g., ortho-, pyro- and/or polyphosphoric acid, phosphoric esters or phosphorous acid), and a reductive alcohol (e.g., isobutanol), isolation of the precipitate, and drying, with shaping (e.g., tableting) where appropriate; and (2) preactivation to give vanadyl pyrophosphate ((VO)$_2$P$_2$O$_7$) by calcining.

Variants and different embodiments of the preparation of the catalyst are described, for example, in U.S. Pat. No. 4,567,158, U.S. Pat. No. 4,996,179, U.S. Pat. No. 5,137,860, U.S. Pat. No. 5,506,187, U.S. Pat. No. 5,530,144 and U.S. Pat. No. 5,773,382.

U.S. Pat. No. 4,567,158 discloses the calcining of the shaped vanadyl phosphate hemihydrate precursor tablets in a forced-draft oven, and describes a one-stage and a two-stage calcining. In one-stage calcining, the precursor tablets are treated at 350° C. under air. In two-stage calcining the precursor tablets are calcined first at from 350 to 400° C. under air and then at from 330 to 500° C. under a nitrogen/steam atmosphere.

U.S. Pat. No. 5,137,860 teaches calcining the shaped vanadyl phosphate hemihydrate precursor tablets on perforated stainless steel plates in a tray oven. For this calcining, the precursor tablets are first treated at a temperature up to 300° C. in an atmosphere containing oxygen, steam, and possibly inert gas, then subjected to a temperature increase to more than 350° C. and less than 550° C., in order to set the oxidation state of the vanadium, after which the temperature treatment is continued under a nonoxidizing atmosphere comprising steam, with a water content of from 25 to 75 mol %.

U.S. Pat. No. 5,773,382 describes the use of pore formers in the preparation of vanadium-phosphorus-oxygen catalysts. The vanadyl phosphate hemihydrate precursor tablets with the pore former in them are first freed from the pore former on metal plates in a tray oven at a temperature of from 165 to 255° C., during which air is supplied, and then calcined in a further tray oven as described in U.S. Pat. No. 5,137,860.

U.S. Pat. No. 4,996,179 teaches the preactivation of a vanadium, phosphorus, and oxygen catalyst precursor powder, obtained by precipitation, evaporative concentration, and drying, said preactivation taking place in air or in a nitrogen/air mixture at from 300 to 370° C. in a rotary tube furnace or fluid-bed furnace. The preactivated catalyst precursor powder obtained is subsequently tableted and calcined at a temperature of from 343 to 704° C. in an inert atmosphere and subsequently at an increased temperature in an oxygenous atmosphere.

U.S. Pat. No. 5,506,187 describes the calcining of a vanadium, phosphorus, and oxygen catalyst precursor powder, obtained by precipitation, evaporative concentration, and drying, said calcining taking place at from 288 to 427° C. in a rotary tube furnace in air or air/steam.

U.S. Pat. No. 5,530,144 teaches the calcining of vanadyl phosphate hemihydrate precursors at a temperature from 350 to 700° C. under nitrogen, air or mixtures thereof in a suitable calcining apparatus. General examples given are fluid-bed furnaces, rotary tube furnaces, and continuously operated muffle furnaces.

It is an object of the present invention to provide a process for preparing a particulate vanadium-phosphorus-oxygen catalyst for the heterogeneously catalyzed gas-phase oxidation of a hydrocarbon having at least four carbon atoms to maleic anhydride that even for tonne-scale production leads to a catalyst which when employed in a shell-and-tube reactor results in a very low spread of the temperatures established in the individual tubes and which therefore permits further optimization with respect to high conversion, high selectivity, high yield, and long catalyst lifetime in combination with a high level of safety in respect of reaction runaway.

We have found that this object is achieved by a process for preparing a vanadium, phosphorus, and oxygen catalyst suitable for heterogeneously catalyzed gas-phase oxidation of a hydrocarbon having at least four carbon atoms to maleic anhydride, in which a corresponding vanadium, phosphorus, and oxygen catalyst precursor containing particles having an averaged diameter of at least 2 mm is converted into a catalytically active form by calcining, which comprises passing a stream of the catalyst precursor for calcining at substantially constant speed through at least one calcining zone n of length $1_n$ on a conveyor belt, the fluctuation in the gas temperature from the setpoint value over time at each point in the region of the stream of the catalyst precursor after half the length of the calcining zone, $1_n/2$, being in each case $\leq 5°$ C. and the local difference in gas temperature between any two points in the region of the stream of the catalyst precursor after half the length of the calcining zone, $1_n/2$, being in each case $\leq 5°$ C.

Essential to the process of the invention is extremely uniform calcining of the vanadium, phosphorus, and oxygen catalyst precursor, especially in respect of the surrounding gas composition, the ambient temperature, and the respective treatment time under these conditions. Such calcining is ensured in accordance with the invention by passing the particulate catalyst precursor at substantially constant speed through at least one calcining zone; and ensuring very constant temperature in space and time within the calcining zone in the region of the stream of the catalyst precursor.

The term calcining generally embraces thermal treatment steps, including evaporation or decomposition of components present in the catalyst precursor, such as the drying or the decomposition of an auxiliary, for instance.

In general, the process of the invention is implemented using what is known as a belt kiln having at least one calcining zone n and a conveyor belt which is passed through the calcining zone at substantially constant speed. The conveyor belt is generally a continuous belt which can be guided horizontally through the calcining zone and features an ascending reversing track at one of its ends and a descending reversing track at its other end. In many cases it is advantageous to provide the ascending and descending reversing tracks and also the return region of the conveyor belt below the calcining zone with a housing. It is appropriate to provide means for applying the particulate catalyst precursor to the conveyor belt in the vicinity of the ascending reversing track and means for removing the calcined catalyst from the conveyor belt at the descending reversing track. An example of a suitable means for applying the precursor is a shaft filled with the particulate catalyst precursor, with the movement of the conveyor belt drawing off a bed of the catalyst precursor having a substantially constant bed thickness beneath the shaft. The shaft advantageously further possesses an adjustable scraper means, i.e., what is known as a weir, which allows the bed height to be set specifically and allows uniform distribution transversely to the conveying direction.

If sufficient gas exchange is ensured and if there is the desired constancy of temperature, the bed height of the catalyst precursor can in principle be selected almost arbitrarily. Generally speaking, the bed height is in the range from one single layer of the catalyst precursor particles up to 25 cm, preferably from 1 to 20 cm, with particular preference from 5 to 15 cm, and with very particular preference from 8 to 15 cm. At the descending reversing track the calcined catalyst is ejected from the conveyor belt and collected by suitable means. The conveyor belt is generally composed of a heat-stable material, metal for example.

The speed at which the conveyor belt is passed through the calcining zone n is generally from about 0.1 to 5 cm/min. With the process of the invention, the speed of the conveyor belt and hence of the stream of the catalyst precursor is substantially constant, the timescale in question lying within the order of magnitude of the residence time of the stream of the catalyst precursor in the chamber n.

In one preferred embodiment, a gas-permeable conveyor belt is used and a gas stream is passed through the stream of the catalyst precursor perpendicularly to its direction of advance in the calcining zone n. The gas-permeable conveyor belt is composed, for example, of a perforated belt, a woven mesh or a knitted mesh of heat-stable material, made for example of metal, such as alloyed steel, for instance.

The calcining zone n is generally in the form of a chamber, i.e., is surrounded by side walls and a top and a bottom wall. The walls present in the conveying direction of the conveyor belt are provided with openings for the passage of the stream of the catalyst precursor.

The chamber can be heated in a variety of ways. For example, it is possible to introduce the requisite heat by supplying heated gas, which, for example, has been taken off from the chamber beforehand and heated by means of a heat source. Another possibility is to heat the chamber n by way of the walls, electrically or by burners, for example. Preferably, heating takes place by means of a burner sited below the chamber and operated, for instance, with natural gas. In order to maximize the uniformity of heat distribution, the combustion space is surrounded by a further wall and is insulated from the outside.

Generally, the temperature in the calcining zone n is measured by ay of temperature measurement points (e.g., thermocouples) and the heating is regulated accordingly.

Since the surrounding gas atmosphere generally has a decisive influence on the properties of the calcined catalyst and since gas may be consumed from the surrounding atmosphere by the calcining process, and gaseous components which form can be given up to the surrounding atmosphere, it is particularly important to set the gas atmosphere specifically by continuously supplying fresh gas and also, in association with this, by continuously taking off what is known as a purge stream. Depending on the desired gas atmosphere, therefore, an appropriate amount of the requisite fresh gas is supplied continuously and a corresponding purge stream is taken off continuously. In order to achieve a very high level of temperature constancy locally and over time, and also to achieve a substantially homogeneous gas atmosphere in the region of the stream of the catalyst precursor, the atmosphere in the chamber of the calcining zone n is preferably circulated.

For this purpose, it is preferred to set up a gas circulation system in the calcining zone n, the volume of gas circulating in the calcining zone n per unit time being greater than the volume of gas supplied freshly to the calcining zone n per unit time.

This gas circulation system can be ensured in a variety of ways. One possibility, for example, is to take off gas from the chamber, preferably from the upper part, using a blower, to pass it where appropriate through a heat exchanger, and to resupply it to the chamber, preferably in the lower part beneath the gas-permeable conveyor belt. In another variant, which is preferred in the context of the process of the invention, the chamber itself comprises means for generating the gas circulation system.

In one particularly preferred embodiment, the means for generating the gas circulation system comprise a fan, which is appropriately arranged above the conveyor belt in the chamber. In suitable embodiments, the means for generating the gas circulation system further comprise gas guide devices for guiding the gas circulation within the chamber, the gas guide devices within the chamber each extending vertically to the surface of the conveyor belt, substantially in one plane, in each case at the edge of the conveyor belt. The means for generating the gas circulation system and/or the gas guide devices are appropriately designed so that the gas ascends through the gas-permeable conveyor belt and through the bed of particulate catalyst precursor present on said belt and descends again at the walls of the chamber. Alternatively, it is possible to conceive of a gas circulation system operating in the opposite direction. Where the belt calcining means has at least two heatable chambers, they are preferably delimited from one another such that there is substantially no gas exchanged between the chambers.

In the process of the invention, the fluctuation in the gas temperature from the setpoint value over time at each point in the region of the stream of the catalyst precursor after half the length of the calcining zone, $1_n/2$, is in each case $\leq 5°$ C. and the local difference in gas temperature between any two points in the region of the stream of the catalyst precursor after half the length of the calcining zone, $1_n/2$, is in each case $\leq 5°$ C.

The constancy of the temperature can be checked by means of temperature measurement points, i.e., preferably thermocouples. For each calcining zone n it is necessary to use preferably at least 4, with particular preference at least 6, and with very particular preference at least 10 temperature measurement points, disposed as far as possible equidistant from one another and distributed over the entire width of the stream of the catalyst precursor in the region of said stream of the catalyst precursor after half the length of the calcining zone, $1_n/2$.

The fluctuation of the gas temperature from the setpoint value over time refers to the amount of the difference between the hourly average, measured at a fixed point x in the region of the stream of the catalyst precursor after half the length of the calcining zone, $1_n/2$, and the setpoint value. The fluctuation of the gas temperature from the setpoint value over time can therefore be expressed as |T(hourly average at point x)−T(setpoint value)|.

The local difference in gas temperature refers to the amount of the difference between the hourly average, measured at a fixed point x and the hourly average, measured at a fixed point y, in each case in the region of the stream of the catalyst precursor, after half the length of the calcining zone, $1_n/2$. The local difference in gas temperature can therefore be expressed as |T(hourly average at point x)−T(hourly average at point y)|.

In the process of the invention, the fluctuation of the gas temperature from the setpoint value over time at any point in the region of the stream of the catalyst precursor after half the length of the calcining zone, $1_n/2$, is preferably in each case $\leq 3°$ C. and with particular preference in each case $\leq 2°$ C.

In the process of the invention, the local difference in gas temperature between any two points in the region of the stream of the catalyst precursor after half the length of the calcining zone, $1_n/2$, is preferably in each case $\leq 3°$ C. and with particular preference in each case $\leq 2°$ C.

The registration of the temperatures measured at the individual thermocouples, and the formation of the averages, are appropriately accomplished in an automated fashion by means of an appropriately programmed computer. Said computer advantageously also performs the regulation or control of the heating of the calcining zones. It is advisable to calibrate the thermocouples regularly in order to ensure that the maximum deviation of the measured temperature from the actual temperature is preferably less than 0.5° C.

The gas atmosphere in the calcining zone n generally comprises oxygen, nitrogen, hydrogen oxide (steam), carbon dioxide, carbon monoxide and/or noble gases. The gas atmosphere may further comprise evaporation and decomposition products of catalyst precursor components, such as pore formers or auxiliaries, for example.

The stream of the catalyst precursor is preferably passed for calcining through at least two—for example, from two to ten—calcining zones, the temperatures and the gas atmospheres of the individual calcining zones being regulatable independently of one another. In this way it is possible to realize different temperature profiles and gas profiles through which the stream of the catalyst precursor passes. For example, the successive calcining zones can be thermostatted to gradually increasing or falling temperatures. In addition, the individual calcining zones may have different spatial extents, thereby resulting in different residence times in the individual calcining zones if the speed of the stream of the particulate catalyst precursor is constant. It is of course also possible to operate adjacent calcining zones at the same temperature and with the same gas atmosphere, in order to obtain a longer residence time, for instance. It is further possible as well, of course, to operate adjacent calcining zones at the same temperature but with a different gas atmosphere.

Depending on the total number of calcining zones desired and the number of calcining zones in a belt calcining means it is also possible where appropriate to operate two or more—for example, two or three—belt calcining means in series. This may also be advantageous, possibly, if different bed heights and/or different residence times are needed in order to optimize the calcining operation, for example. Where appropriate, the catalyst precursor may be collected and stored after passing through one belt calcining means and before passing through another.

One preferred embodiment of a belt calcining means which can be used with preference for the process of the invention is illustrated schematically by the attached drawings.

FIG. 1 shows a longitudinal section and

Figure 2:
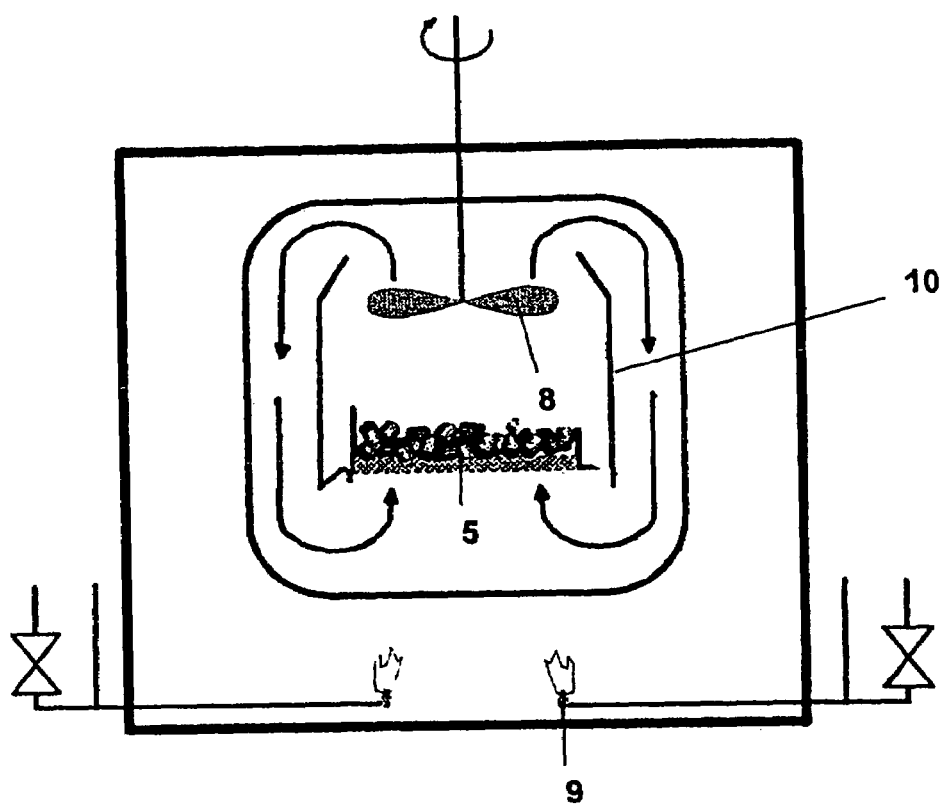

FIG. 2 a cross section through the preferred belt calcining means.

Referring to FIG. 1, the belt calcining means depicted has four enchambered calcining zones (1, 2, 3, 4) traversed by a gas-permeable conveyor belt (5). The belt calcining means further comprises a bunker (6) with an adjustable weir (7). Above the conveyor belt (5) in each chamber there are one or more fans (8). Each chamber is provided with air supply and air removal means (9). In operation, the bunker (6) is filled with the particulate catalyst precursor. Beneath the weir (7), a bed of the catalyst precursor with a constant height is drawn off by the movement of the conveyor belt (5) and passes in succession through the chambers of the belt calcining means.

Referring to FIG. 2, each chamber is heated by one or more burners (9). Meta gas die plates (10) are arranged perpendicularly to the surface of the conveyor belt, substantially in one plane, at the edges of the conveyor belt, and together with the fans (8) ensure that the circulated atmosphere in every chamber ascends through the gas-permeable conveyor belt (5) and descends again at the walls of the chamber.

The catalyst precursors which can be used for the process of the invention comprise as their catalytically active material an oxygenous vanadium phosphorus compound or mixtures of such compounds. Suitable active materials are described, for example, in patents U.S. Pat. No. 5,275,996, U.S. Pat. No. 5,641,722, U.S. Pat. No. 5,137,860, U.S. Pat. No. 5,095,125, and U.S. Pat. No. 4,933,312.

They may further comprise what are known as promoters. Suitable promoters are the elements from groups 1 to 15 of the periodic system and also their compounds. Suitable promoters are described, for example, in the OPI documents WO 97/12674 and WO 95/26817 and also in patents U.S. Pat. No. 5,137,860, U.S. Pat. No. 5,296,436, U.S. Pat. No. 5,158,923, and U.S. Pat. No. 4,795,818. Preferred promoters are compounds of the elements cobalt, molybdenum, iron, zinc, hafnium, zirconium, lithium, titanium, chromium, manganese, nickel, copper, boron, silicon, antimony, tin, niobium, and bismuth, with particular preference molybdenum, iron, zinc, antimony, bismuth and lithium. The promoted catalysts may comprise one or more promoters. The promoter content is generally not more than about 5% by weight of the finished catalyst, calculated in each case as the oxide.

As a result of the preceding preparation of the catalyst precursor it may further comprise auxiliaries, such as tableting auxiliaries or pore formers, for instance.

tableting aids are generally added when the catalyst of the invention is shaped by tableting. tableting aids are generally catalytically inert and enhance the tableting properties of the precursor powder, an intermediate in the catalyst preparation process, by raising the sliding and free-flow properties, for example. One suitable and preferred tableting aid is graphite. The tableting aids generally remain in the activated catalyst. The tableting aid content of the finished catalyst is typically from about 2 to 6% by weight.

Pore formers are substances which are used for setting a specific pore structure in the macropore range. In principle they can be used independently of the shaping process. Generally speaking they are carbon, hydrogen, oxygen and/or nitrogen compounds which are added prior to shaping of the catalyst and are predominantly removed again-by sublimation, decomposition and/or vaporization during the subsequent activation of the catalyst. Nevertheless, the finished catalyst may include residues or decomposition products of the pore former.

The catalyst precursors which can be used in the process of the invention may comprise the active material, for example, in pure, undiluted form as an "all-active catalyst precursor" or diluted with a preferably oxidic support material as a "mixed catalyst precursor". Examples of suitable support materials for mixed catalysts include aluminum oxide, silicon dioxide, aluminosilicates, zirconium dioxide, titanium dioxide, and mixtures thereof. The preparation of all-active and mixed catalysts is preferred, that of all-active catalysts particularly preferred.

The catalyst precursor which can be used in the process of the invention comprises particles having an averaged diameter of at least 2 mm, preferably at least 3 mm. The averaged diameter of a particle is the average of the smallest and the largest dimension between two plane-parallel plates.

By particles are meant both irregularly shaped particles and geometrically shaped particles, i.e., moldings. The catalyst precursor for use in the process of the invention preferably comprises moldings. Examples of suitable moldings that may be mentioned include tablets, cylinders, hollow cylinders, beads, strands, wagon wheels or extrudates. Special forms, such as trilobes and tristars (see EP-A-0 593 646) or moldings having at least one notch in the outside (see U.S. Pat. No. 5,168,090), for example, are likewise possible.

With particular preference, the catalyst precursor which can be used in the process of the invention comprises moldings having a substantially hollow cylindrical structure. A substantially hollow cylindrical structure is a structure which substantially comprises a cylinder with an orifice passing between the two end faces. The cylinder is characterized by two substantially parallel end faces and a lateral surface, the cross section of the cylinder, i.e., parallel to the end faces, being substantially of circular structure. The cross section of the continuous orifice, i.e., parallel to the end faces of the cylinder, is substantially likewise of circular structure. Preferably, the continuous orifice is concentric with respect to the end faces, although other spatial arrangements are not excluded by this.

The term "substantially" indicates that deviations from the ideal geometry, such as slight deformations of the circular structure, end faces which are not in plane-parallel alignment, flaked-off angles and edges, surface roughness or notches in the lateral surface, the end faces or the inner surface of the continuous hole, are embraced in the catalyst precursor. With regard to the accuracy of the tableting art, circular end faces, a circular cross section of the continuous hole, end faces in parallel alignment, and macroscopically smooth surfaces are preferred.

A substantially hollow cylindrical structure can be described by an external diameter $d_1$, a height h as the distance between the two end faces, and an inner hole (continuous orifice) diameter $d_2$. The external diameter $d_1$ of the catalyst precursor is preferably from 3 to 10 mm, with particular preference from 4 to 8 mm, with very particular preference from 4.5 to 6 mm. The height h is preferably from 1 to 10 mm, with particular preference from 2 to 6 mm, with very particular preference from 2 to 3.5 mm. The continuous orifice diameter $d_2$ is preferably from 1 to 8 mm, with particular preference from 2 to 6 mm, with very particular preference from 2 to 3 mm.

The catalyst precursor which can be used in the process of the invention may be prepared as described, for example, in patents U.S. Pat. No. 5,275,996 and U.S. Pat. No. 5,641,722 or in the OPI document WO 97/12674. The key steps of one preferred catalyst precursor preparation are elucidated below.

(a) Reaction of a pentavalent vanadium compound (e.g., $V_2O_5$) and where appropriate a promoter component (e.g., $MoO_3$) with an organic, reducing solvent (e.g. an alcohol, such as isobutanol) in the presence of a pentavalent phosphorus compound (e.g., ortho- and/or pyrophosphoric acid, phosphates) and/or a trivalent phosphorus compound (e.g., phosphorous acid), with heating. Where appropriate, this stage can be carried out in the presence of a dispersed pulverulent support material. The reaction without the addition of support material is preferred.

(b) Isolation of the resultant catalyst precursor comprising vanadium, phosphorus, oxygen, and promoter if desired—VPO precursor—by filtration or evaporative concentration, for example.

(c) Drying of the VPO precursor and preferably incipient preactivation by heat treatment at a temperature from 250 to 350° C. Where appropriate, pulverulent support material and/or a pore former, such as stearic acid, cellulose or paraffins, for example, can be mixed with the dried and preferably heat-treated VPO precursor powder. Further processing without the addition of a support material and without the addition of a pore former is preferred.

(d) Shaping by conversion into the desired structure, preferably into the substantially hollow cylindrical structure. Shaping takes place preferably by tableting, advantageously with the prior admixing of a lubricant, such as graphite.

One example of an alternative to tableting, albeit a less preferred one, is extrusion. In this variant, for example, the VPO precursor obtained in (b) is pasted up to give an extrudable material. This material can then be extruded into the desired structure and dried to give the catalyst precursor in a usable form.

In the process of the invention, the catalyst precursor is calcined in the presence of an atmosphere comprising oxygen, hydrogen oxide (steam) and/or inet gas in a temperature range from 250 to 600° C. Examples of suitable inert gases include nitrogen, carbon dioxide, and noble gases. For calcining in the process of the invention it is preferred to traverse at least two calcining zones, from two to ten calcining zones for example, with different gas atmospheres and also, where appropriate, different temperatures. By means of a suitable combination of temperatures, treatment times, and gas atmospheres, adapted to the particular catalyst system, it is possible to influence and hence tailor the mechanical and catalytic properties of the catalyst.

The process of the invention prefers a calcining operation wherein the catalyst precursor (a) is heated to a temperature of from 200 to 350° C. in at least one calcining zone in an oxidizing atmosphere having an oxygen content of from 2 to 21% by volume and is left under these conditions until the desired average oxidation state of the vanadium is reached; and (b) is heated to a temperature of from 300 to 500° C. in at least one further calcining zone in a nonoxidizing atmosphere having an oxygen content of $\leq 0.5\%$ by volume and a hydrogen oxide content of from 20 to 75% by volume and is left under these conditions for $\geq 0.5$ hour.

In step (a) the catalyst precursor is left in an oxidizing atmosphere having a molecular oxygen content of generally from 2 to 21% by volume and preferably from 5 to 21% by volume at a temperature from 200 to 350° C. and preferably from 250 to 350° C. for a period which is effective to set the desired average oxidation state of the vanadium. Generally in step (a) mixtures of oxygen, inert gases (e.g., nitrogen or argon), hydrogen oxide (steam) and/or air, and also air itself, are used. From the standpoint of the catalyst precursor passed through the calcining zone or zones, the temperature during calcining step (a) may be kept constant or may on average rise or fall. Since step (a) is generally preceded by a heating phase, the temperature will generally first of all rise before then leveling off at the desired end value. Generally, therefore, at least one further calcining zone for the heating of the catalyst precursor is included upstream of the calcining zone of step (a).

In the process of the invention, the period over which the heat treatment in step (a) is maintained is chosen preferably so as to set an average oxidation state of the vanadium at a level of from +3.9 to +4.4, preferably from +4.0 to +4.3. The average oxidation state of the vanadium is determined by potentiometric titration in accordance with the method described in the examples.

Since for reasons associated with apparatus and with time it is extremely difficult to determine the average oxidation state of the vanadium during the calcining operation, the requisite period must advantageously be determined in preliminary experiments. This purpose is generally served by a series of measurements in which heat treatment is carried out under defined conditions and the samples are removed from the system at different times, cooled, and analyzed in respect of the average oxidation state of the vanadium.

The period required in step (a) is generally dependent on the nature of the catalyst precursor, on the set temperature, and on the chosen gas atmosphere, particularly the oxygen content. The period for step (a) generally extends to a duration of more than 0.5 hour and preferably of more than 1 hour. Generally speaking, a period of up to 4 hours, preferably of up to 2 hours, is sufficient for setting the desired average oxidation state. Under correspondingly adjusted conditions (e.g., lower region of the temperature range and/or low molecular oxygen content), however, a period of more than 6 hours may also be necessary.

In step (b), the resultant catalyst intermediate is left over a period of $\geq 0.5$ hour, preferably from 2 to 10 hours, and with particular preference from 2 to 4 hours in a nonoxidizing atmosphere having a molecular oxygen content of $\leq 0.5\%$ by volume and a hydrogen oxide (steam) content of from 20 to 75% by volume, preferably 30 to 60% by volume, at a temperature from 300 to 500° C. and preferably from 350 to 450° C. In addition to said hydrogen oxide, the nonoxidizing atmosphere generally contains predominantly nitrogen and/or noble gases, such as argon, for example, albeit with no restriction being intended. Gases such as carbon dioxide, for example, are also suitable in principle. The nonoxidizing atmosphere preferably contains ≧40% by volume nitrogen. From the standpoint of the catalyst precursor which is passed through the calcining zone or zones, the temperature during calcining step (b) may be kept constant or may on average rise or fall. Where step (b) is conducted at a higher or lower temperature than step (a), there is generally a heating or cooling phase between steps (a) and (b), implemented where appropriate in a further calcining zone. In order to permit improved separation from the oxygenous atmosphere of step (a), said further calcining zone may be purged with inert gas, such as nitrogen, for example, between (a) and (b). Step (b) is preferably conducted at a temperature higher than step (a) by from 50 to 150° C.

The calcining operation generally comprises a further step, (c), conducted later than step (b), in which the calcined catalyst precursor is cooled to a temperature of ≦300° C., preferably ≦200° C., and with particular preference ≦150° C. in an inert gas atmosphere.

Before, during and/or after steps (a) and (b), or (a), (b), and (c), further steps are possible when calcining in accordance with the process of the invention. Without limitation, examples that may be mentioned of further steps include changes in temperature (heating, cooling), changes in gas atmosphere (changeover of the gas atmosphere), further holdup times, transfers of the catalyst intermediate to other apparatus, or interruptions in the overall calcining operation.

Since the catalyst precursor generally possesses a temperature of <100° C. before calcining commences, it must normally be heated prior to step (a). Heating can be carried out using different gas atmospheres. Heating preferably takes place in an oxidizing atmosphere as defined in step (a) or in an inert gas atmosphere as defined in step (c). A change in gas atmosphere during the heating phase is a further possibility. Particular preference is given to heating in the oxidizing atmosphere which is also employed in step (a).

The catalyst prepared preferably by the process of the invention has a phosphorus/vanadium atomic ratio of from 0.9 to 1.5, with particular preference from 0.9 to 1.2, and with very particular preference from 1.0 to 1.1, an average vanadium oxidation state of from +3.9 to +4.4 and with particular preference from 4.0 to 4.3, a BET surface area of from 10 to 50 m$^2$/g and with particular preference from 20 to 40 m$^2$/g, a pore volume of from 0.1 to 0.5 ml/g and with particular preference from 0.2 to 0.4 ml/g, and a bulk density of from 0.5 to 1.5 kg/l and with particular preference from 0.5 to 1.0 kg/l.

The invention further provides a process for preparing maleic anhydride by heterogeneously catalyzed gas-phase oxidation of a hydrocarbon having at least four carbon atoms with oxygenous gases, which comprises using a catalyst of the invention as described above.

In the process of the invention for preparing maleic anhydride, use is generally made of shell-and-tube reactors. Suitable hydrocarbons generally include saturated and unsaturated, aliphatic and aromatic hydrocarbons having at least four carbon atoms, such as 1,3-butadiene, 1-butene, 2-cis-butene, 2-trans-butene, n-butane, C$_4$ mixture, 1,3-pentadiene, 1,4-pentadiene, 1-pentene, 2-cis-pentene, 2-trans-pentene, n-pentane, cyclopentadiene, dicyclopentadiene, cyclopentene, cyclopentane, C$_5$ mixture, hexenes, hexanes, cyclohexane, and benzene. Preference is given to using 1-butene, 2-cis-butene, 2-trans-butene, n-butane, benzene or mixtures thereof. Particular preference is given to using n-butane and liquids and gases comprising it. The n-butane used may originate, for example, from natural gas, from steam crackers or from FCC crackers.

The hydrocarbon is generally added in a flow-regulated manner, i.e., with continual setting of a defined amount per unit time. The hydrocarbon can be metered in liquid or gaseous form. It is preferably metered in liquid form with subsequent vaporization before entering the shell-and-tube reactor.

Oxidants used are gases comprising oxygen, such as air, synthetic air, an oxygen-enriched gas, or else what is termed "pure" oxygen, i.e., oxygen originating from air fractionation, for example. The oxygenous gas is also added in a flow-regulated manner.

The gas to be passed through the shell-and-tube reactor generally has a hydrocarbon concentration of from 0.5 to 15% by volume and an oxygen concentration of from 8 to 25% by volume. The remaining fraction, to 100% by volume, is composed of further gases such as nitrogen, noble gases, carbon monoxide, carbon dioxide, steam, oxygenated hydrocarbons (e.g., methanol, formaldehyde, formic acid, ethanol, acetaldehyde, acetic acid, propanol, propionaldehyde, propionic acid, acrolein, and crotonaldehyde) and mixtures thereof. The amount of n-butane as a fraction of the total amount of hydrocarbon is preferably ≧90% and with particular preference ≧95%.

To ensure a long catalyst life and to further increase conversion, selectivity, yield, space velocity over the catalyst, and space-time yield, the process of the invention prefers adding a volatile phosphorus compound to the gas. The concentration of this compound at the beginning, i.e., at the entrance to the reactor, is at least 0.2 ppm by volume, i.e., $0.2 \cdot 10^{-6}$ parts by volume of the volatile phosphorus compounds relative to the total volume of the gas at the reactor entrance. Preference is given to an amount of from 0.2 to 20 ppm by volume, with particular preference from 0.5 to 10 ppm by volume. Volatile phosphorus compounds are all phosphorus compounds which are present in gaseous form at the desired concentration under the conditions of use. Examples of suitable volatile phosphorus compounds are phosphines and phosphates. Particular preference is given to the C$_1$ to C$_4$ alkyl esters of phosphoric acid, with very particular preference trimethyl phosphate, triethyl phosphate and tripropyl phosphate, and especially triethyl phosphate.

The process of the invention is generally conducted at a temperature from 350 to 480° C. The temperature specified here is the temperature at which the catalyst bed in the shell-and-tube reactor would be were the process to be practiced in the absence of a chemical reaction. If this temperature is not exactly the same at every point, the term refers to the numerical average of the temperatures along the reaction zone. In particular, this means that the true temperature at the catalyst may even be outside the abovementioned range as as result of the exothermic nature of the oxidation reaction. The process of the invention is preferably conducted at a temperature from 380 to 460° C., with particular preference from 380 to 430° C.

The process of the invention may be performed at a pressure below atmospheric pressure (e.g., down to 0.05 MPa abs) or else above atmospheric pressure (e.g., up to 10 MPa abs). The pressure referred to is the pressure prevailing in the shell-and-tube reactor unit. The pressure is preferably from 0.1 to 1.0 MPa abs, with particular preference from 0.1 to 0.5 MPa abs.

The process of the invention can be carried out in two preferred variants, namely the "straight pass" variant and the "recirculation" variant. In the straight pass variant, maleic anhydride and any oxygenated hydrocarbon byproducts are removed from the reactor discharge and the remaining gas mixture is separated off and possibly utilized for generating heat. In the recirculation variant, maleic anhydride and any oxygenated hydrocarbon byproducts are likewise removed from the reactor discharge, but some or all of the remaining gas mixture, which includes unreacted hydrocarbon, is recirculated to the reactor. Another variant of the recirculation mode is the removal of the unreacted hydrocarbon and its recirculation to the reactor.

In one particularly preferred embodiment for the preparation of maleic anhydride, n-butane is used as starting hydrocarbon and the heterogeneously catalyzed gas-phase oxidation is carried out in a straight pass over the catalyst of the invention.

In one particularly preferred embodiment of the process of the invention for preparing a vanadium, phosphorus, and oxygen catalyst suitable for the heterogeneously catalyzed gas-phase oxidation of a hydrocarbon having at least four carbon atoms to maleic anhydride, a catalyst precursor is used which comprises vanadyl hydrogen phosphate hemihydrate ($VOHPO_4 \cdot \frac{1}{2}H_2O$) and has been obtained by heating a vanadium(V) compound, preferably vanadium pentoxide, and phosphoric acid, preferably phosphoric acid with a concentration of from 100 to 110%, under reflux, filtering off, washing, and drying the resultant precipitate, treating it in an oxygenous atmosphere at a temperature in the range from 80 to 350° C., preferably from 200 to 250° C., over a period of from 1 to 8 hours, and tableting the product to the desired form.

The catalyst precursor is then supplied to a belt calcining means and, by way of a corresponding metering means with adjustable weir, is applied at a constant bed height in the range from 5 to 15 cm to a gas-permeable conveyor belt. The gas-permeable conveyor belt is passed at a substantially constant speed in the range from 0.1 to 5 cm/min through the individual calcining zones. The belt calcining means used with preference comprises at least 5, in particular from 6 to 8, calcining zones which are operated at different temperatures and/or with different gas atmospheres. Each calcining zone is enchambered and equipped with one or more fans and also an air supply and air removal means. Fresh gas is continuously supplied and a corresponding amount of purge gas is continuously taken off. The volume of the gas circulating in the calcining zone n per unit time is in each case greater than the volume of gas supplied to the calcining zone n per unit time.

The parameter ranges within which the belt calcining means used with preference, with 8 calcining zones, is preferably operated are shown in Table 1.

TABLE 1

Parameter ranges for the preferred calcining.

| Zone | Temperature | Fresh gas supplied | Average residence time |
|---|---|---|---|
| Calcining zone 1 | Heating to a temperature in the range from 150 to 250° C. | Air or air/$N_2$ | From 1 to 3 hours |
| Calcining zone 2 | Conditioning at from 150 to 250° C. | Air or air/$N_2$ | From 1 to 3 hours |
| Calcining zone 3 | Conditioning at from 150 to 250° C. | Air or air/$N_2$ | From 1 to 3 hours |
| Calcining zone 4 | Heating to a temperature in the range from 250 to 350° C. | Air or air/$N_2$ | From 1 to 3 hours |
| Calcining zone 5 | Heating to a temperature in the range from 250 to 450° C. | $N_2$ | From 1 to 3 hours |
| Calcining zone 6 | Conditioning at from 350 to 450° C. | $N_2$/steam | From 1 to 3 hours |
| Calcining zone 7 | Conditioning at from 350 to 450° C. | $N_2$/steam | From 1 to 3 hours |
| Calcining zone 8 | Cooling to room temperature | $N_2$ | From 1 to 3 hours |

Where a belt calcining means having 5, 6 or 7 calcining zones is used, the abovementioned steps 1+2, 2+3, 1+2+3 and/or 6+7 are condensed.

The fluctuation of the gas temperature from the setpoint value over time at any point in the region of the stream of the catalyst precursor after half the length of the calcining zone, $1_n/2$, is preferably in each case $\leq 5°$ C. in calcining zones 2, 3, 4, 6, and 7 and with particular preference in all calcining zones, and the local difference in gas temperature between any two points in the region of the stream of the catalyst precursor after half the length of the calcining zone, $1_n/2$, is preferably in each case $\leq 5°$ C. in calcining zones 2, 3, 4, 6, and 7 and with particular preference in all calcining zones.

The process of the invention allows high-quality production of a particulate vanadium-phosporus-oxygen catalyst for the heterogeneously catalyzed gas-phase oxidation of a hydrocarbon having at least four carbon atoms to maleic anhydride, said process being suitable for continuous implementation starting from a particulate catalyst precursor comprising vanadium, phosphorus, and oxygen, and yielding relatively large amounts, on the metric ton scale, throughout the production operation, to give a highly uniform catalyst with a very low spread of catalytic, mechanical, physical, and chemical properties. When used in a shell-and-tube reactor, the catalyst prepared in accordance with the invention leads to a very low spread of the temperatures which are established in the individual tubes and so makes it possible to achieve further optimization in respect of high conversion, high hydrocarbon velocity, high selectivity, high yield, and long catalyst lifetime in combination with a high level of security in respect of the runaway of the reaction.

DEFINITIONS

Unless mentioned otherwise, the variables used in this text are defined as follows:

$$\text{Space-time yield} = \frac{m_{maleic\ anhydride}}{V_{catalyst} \cdot t}$$

$$\text{Space velocity} = \frac{V_{hydrocarbon}}{V_{catalyst} \cdot t}$$

$$\text{Conversion U} = \frac{n_{HC,\ reactor,\ in} - n_{HC,\ reactor,\ out}}{n_{HC,\ reactor,\ in}}$$

$$\text{Selectivity } S = \frac{n_{MAN,\ reactor,\ out}}{n_{HC,\ reactor,\ in} - n_{HC,\ reactor,\ out}}$$

$$\text{Yield } A = U \cdot S$$

$m_{maleic\ anhydride}$ mass of maleic anhydride produced [g]
$V_{catalyst}$ Bulk volume of catalyst summated over all reaction zones [L]
t Time unit [h]
$V_{hydrocarbon}$ volume of hydrocarbon in the gas phase, standardized to 0° C. and 0.1013 MPa [L(stp)](Arithmetic variable. Where a hydrocarbon is in the liquid phase under these conditions, the hypothetical gas volume is calculated using the ideal gas law.)
U Conversion of hydrocarbons per reactor pass
S Selectivity for maleic anhydride per reactor pass
A Yield of maleic anhydride per reactor pass
$n_{HC,\ reactor,\ in}$ Volume flow in hydrocarbons at the reactor entry [mol/h]
$n_{HC,\ reactor,\ out}$ Volume flow in hydrocarbons at the reactor exit [mol/h]
$n_{HC,\ plant,\ in}$ Volume flow in hydrocarbons at the plant entry [mol/h]
$n_{HC,\ plant,\ out}$ Volume flow in hydrocarbons at the plant exit [mol/h]
$n_{MAN,\ reactor,\ out}$ Volume flow of maleic anhydride at the reactor exit [mol/h]
$n_{MAN,\ plant,\ out}$ Volume flow of maleic anhydride at the plant exit [mol/h]

EXAMPLES

Determination of the Average Oxidation State of the Vanadium

The average oxidation state of the vanadium was determined by potentiometric titration.

For the determination, in each case from 200 to 300 mg of the sample are added under an argon atmosphere of 15 mL of 50% strength sulfuric acid and 5 mL of 85% strength phosphoric acid and are dissolved with heating. The solution is then transferred to a titration vessel which is equipped with two Pt electrodes. The titrations are conducted in each case at 80° C. First, a titration is carried out with 0.1 molar potassium permanganate solution. If two steps are obtained in the potentiometric curve, the vanadium was present in an average oxidation state of from +3 to less than +4. If only one step is obtained, the vanadium was present in an oxidation step of from +4 to less than +5.

In the first-mentioned case (two steps/+3≦$V_{ox}$≦+4), the solution contains no $V^{5+}$, i.e., all of the vanadium was detected titrimetrically. The amount of $V^{3+}$ and $V^{4+}$ is calculated from the consumption of 0.1 molar potassium permanganate solution and the position of the two steps. The weighted average then gives the average oxidation state.

In the second-mentioned case (one step/+4≦$V_{ox}$≦+5), the amount of $V^{4+}$ can be calculated from the consumption of 0.1 molar potassium permanganate solution. By then reducing all of the $V^{5+}$ in the resulting solution with a 0.1 molar ammonium iron(II) sulfate solution and further oxidation with 0.1 molar potassium permanganate solution, the total amount of vanadium can be calculated. The difference between the total amount of vanadium and the amount of $V^{4+}$ gives the amount of $V^{5+}$ originally present. The weighted average then gives the average oxidation state.

Determination of the Lateral Compressive Strength of the Hollow Cylinders

In order to determine the lateral compressive strength, in successive measurements the hollow cylinders were each placed with the rounded side face on the planar metal platform of a corresponding measurement means. The two plane-parallel end faces were therefore in the vertical direction. A planar metal die was then run onto the hollow cylinder at a rate of advance of 1.6 mm/min and the progress of the action of force on the hollow cylinder was recorded over time until it fractured. The lateral compressive strength of the individual hollow cylinder corresponds to the maximum acting force.

In order to determine the lateral compressive strength, 30 individual measurements were conducted in each case and the average was formed.

Determination of the Geometric Density

The geometric density of the hollow cylinders is defined as the ratio of the mass to the geometric volume of the hollow cylinders. The geometric volume is evident from the external, macroscopic dimensions of the hollow cylinder, taking into account the external diameter, the height, and the diameter of the inner hole.

A statistically viable quantity of hollow cylinders was measured in order to determine the geometric density: their mass was found and the geometric density was determined arithmetically.

Determination of the Mechanical Stability Through a Fall Test

In order to determine the mechanical stability by the fall test, about 50 g of geometrically intact, dedusted hollow cylinders were allowed to fall through a 6.5 m tube with an internal diameter of 21 mm and were collected in a porcelain dish at the end of the tube. The amount collected was subsequently sorted by hand and the mass fraction of the damaged hollow cylinders (hollow cylinders with cracks or flaked-off edges, disintegrated hollow cylinders, fragments, splinters) was determined. The rejects according to this fall test are then given by the ratio of the mass of the damaged hollow cylinders to the original mass.

Determination of the Abrasion

In order to determine the abrasion, about 50 g of dedusted hollow cylinders were placed in a Plexiglas drum having an internal diameter of 290 mm, a height of 40 mm, and a circularly curved (radius: 80 mm) Plexiglas insert which is located between the axis of rotation and the outer wall, is fixedly connected to the Plexiglas drum and spans the entire drum height of 40 mm. The Plexiglas drum, whose axis of rotation was in the horizontal direction, was then rotated at 25 revolutions per minute for 18 minutes. The abraded material of the sample was then sieved off and the remaining particles were dedusted and weighed again. The abrasion is then given by the ratio of the mass loss to the original mass.

Experimental Plant

The experimental plant was equipped with a supply unit and a reactor tube. On the laboratory scale or pilot plant scale, replacing a shell-and-tube reactor by a reactor tube is a very good possibility, provided the dimensions of the reactor tube are situated within the range of an industrial reactor tube. The plant was operated in straight pass mode.

The hydrocarbon was added under flow control in liquid form via a pump. As the oxygenous gas, air was added under flow control. Triethyl phosphate (TEP) was added in liquid form, in solution in water, likewise under flow control.

The shell-and-tube reactor unit consisted of a shell-and-tube reactor with one reactor tube. The length of the reactor tube was 6.5 m, the internal diameter 22.3 mm. Inside the reactor tube there was a protective tube with an outer diameter of 6 mm which housed a multiple thermocouple having 20 temperature measurement points. The reactor tube was surrounded by a thermostatable heat transfer medium circuit and was flow-traversed from top to bottom by the reaction gas mixture. The top 0.3 m of the reactor tube was filled with inert material and constituted the preheating zone. The reaction zone contained in each case 2.2 L of catalyst. The heat transfer medium used was a salt melt.

Gaseous product was taken directly after the shell-and-tube reactor unit and passed to the online gas chromatograph for analysis. The mainstream of the gaseous reactor discharge was removed from the plant.

The plant was operated as follows:

| | |
|---|---|
| Concentration of = n-butane at reactor entry | 2.0% by volume |
| WHSV = | 2000 L(stp)/$L_{catalyst}$ · h |
| Pressure at the reactor entry = | 0.2 MPa abs |
| Concentration of = triethyl phosphate (TEP) | 2 ppm by volume |
| Concentration of steam = | 1.5% by volume |

Preparation of the catalyst Precursor 6.1 m³ of isobutanol were charged to an 8 m³ steel/enamel stirred tank which had been rendered inert using nitrogen, was heated externally using pressurized water, and was fitted with flow disruptors. After the three-stage impellor stirrer had been started up, the isobutanol was heated to 90° C. under reflux. The addition of 736 kg of vanadium pentoxide was then commenced at this temperature, using the conveying screw. When about ⅔ of the desired amount of vanadium pentoxide had been added, after about 20 minutes, the addition of vanadium pentoxide was continued but accompanied by the pumped introduction of 900 kg of 105% strength phosphoric acid. The pump was cleaned by passing a further 0.2 m³ of isobutanol through it. The reaction mixture was subsequently heated at about 100 to 108° C. under reflux and was left under these conditions for 14 hours. Thereafter, the hot suspension was drained off into a heated pressure suction filter which had been rendered inert with nitrogen beforehand and was filtered at a temperature of approximately 100° C. under a pressure above the suction filter of up to 0.35 MPa abs. The filter cake was blown dry over the course of about one hour by continuous introduction of nitrogen at 100° C., with stirring using a centrally arranged, height-adjustable stirrer. After the dry blowing, the product was heated to about 155° C., and evacuated to a pressure of 15 kPa abs (150 mbar abs). Drying was carried out until the dried catalyst precursor had a residual isobutanol content of <2% by weight.

The dried powder was subsequently treated for 2 hours under air in a rotary tube having a length of 6.5 m, an internal diameter of 0.9 m, and internal spiral coils. The rotary speed of the rotary tube was 0.4 rpm. The powder was conveyed into the rotary tube in a quantity of 60 kg/h. The air supply was 100 m³/h. The temperatures of the five heating zones (which were of equal length), measured directly on the outside of the rotary tube, were 250° C., 300° C., 340° C., 340° C. and 340° C. After cooling to room temperature, the VPO precursor was intimately mixed with 1% by weight of graphite and the mixture was compacted in a roll compactor. The fines in the compacted product, with a particle size<400 µm, were sieved off and passed back for compaction. The coarse material, with a particle size≧400 µm, was mixed with a further 2% by weight of graphite and the mixture was tableted in a tableting machine to give 5×3×2.5 mm hollow cylinders (external diameter x height x diameter of the inner hole) having a lateral compressive strength of 11 N. A number of batches were run in order to obtain the amount of catalyst precursor required.

Example 1

Continuous Calcination of the Catalyst Precursor (in Accordance with the Invention)

Approximately 2.7 t of the resulting 5×3×2.5 mm hollow cylinders (see "Preparation of the catalyst precursor") were applied continuously in a bed height of from 9 to 10 cm to the gas-permeable conveyor belt of a belt calcining means comprising two identical belt calcining kilns, in series, with a total of eight calcining zones. The first 1.4 t were used for one-off setting of the operating parameters of the belt calcining means. Since they did not constitute a uniform material, they have not been taken into account any further below.

The belt calcining means was operated at atmospheric pressure. Between calcining zones 4 and 5 there was an encapsulated transition zone. Each of the eight calcining zones included one fan in order to generate a gas circulation. Each of the eight calcining zones was supplied with the desired amount of desired fresh gas. In order to give the desired atmospheric pressure, a corresponding amount of gas was taken off. The volume of gas circulated in each calcining zone per unit time was greater than the volume of gas supplied or taken off per unit time. In order to reduce the level of gas exchange, there was a partition wall between each two successive calcining zones, which was open in the region of the stream of the catalyst precursor. The length of each calcining zone, $1_n$, was 1.45 m. The speed of the conveyor belt was set in accordance with the desired residence time of approximately 2 hours per calcining zone. The individual zones were operated as shown in Table 2:

TABLE 2

Parameters for operation of the belt calcining means.

| Zone | Temperature | Fresh gas supplied |
|---|---|---|
| Calcining zone 1 | Heating to 250° C. | Air |
| Calcining zone 2 | Holding at 250° C. | Air |
| Calcining zone 3 | Holding at 250° C. | Air |
| Calcining zone 4 | Heating to 310° C. | Air |
| Transition zone | Cooling to 200° C. | Air |
| Calcining zone 5 | Heating to 425° C. | $N_2$ |
| Calcining zone 6 | Holding at 425° C. | $N_2$/steam (1:1) |
| Calcining zone 7 | Holding at 425° C. | $N_2$/steam (1:1) |
| Calcining zone 8 | Cooling to room temperature | $N_2$ |

Within all eight calcining zones, the fluctuation in gas temperature over time at each point in the region of the stream of the catalyst precursor after half the length of the calcining zone, $1_n/2$, was in each case ≦1.2° C. and the local difference in gas temperature between any two points in the region of the stream of the catalyst precursor after half the length of the calcining zone, $1_n/2$, was in each case ≦1.5° C. In this way, about 1.3 t of finished catalyst were produced continuously.

At given intervals during the production process, samples of the finished catalyst were taken and were analyzed for the average oxidation state of the vanadium, for the lateral compressive strength, and for the geometric density. The results obtained are reproduced in Table 3.

As can be seen from the results, the process of the invention makes it possible to manage reliably the parameter of the average oxidation state of the vanadium, which is an important parameter for setting the activity and selectivity of the catalyst, within a very narrow range. With an average of 4.16, the lowest value measured was 4.14 and the highest 4.17.

The lateral compressive strength and the geometric density as well were maintained within narrow limits of from 8.4 to 11.4 N, with an average of 10.1 N, and from 1.51 to 1.58 g/mL, with an average of 1.55 g/mL, respectively. The low reject rate after the fall test, and the measured abrasion are likewise confirmation of the narrow range of spread.

Example 2

Catalytic Test of the Catalyst from Example 1

Using a representatively selected individual sample of 2.2 L of the catalyst from Example 1, produced in accordance with the invention, a catalytic performance test was conducted in the experimental plant described above. The salt bath temperature was set so as to give an n-butane conversion of approximately 85%. The results obtained are reproduced in Table 5.

Example 3

Batchwise Calcination of the Catalyst Precursor (Comparative Example)

About 0.4 t of the resulting 5×3×2.5 mm hollow cylinders (see "Preparation of the catalyst precursor") was applied in a bed height of from 4 to 5 cm to gas-permeable metal trays measuring 0.5×1 m in a tray oven. This tray oven comprised a total of ten trays in two adjacent rows and was equipped with an external gas circulation system. The gas, removed beforehand and enriched with the desired amount of fresh gas, was passed into the tray oven from the side. Gas removal was continuous and took place centrally on the top face of the tray oven. The desired amount of fresh gas was supplied continuously to the withdrawn gas, and then the mixture was passed through a heat exchanger and a blower and as described above was passed back to the tray oven from the side. The tray oven was operated at a slight overpressure of 3 kPa (30 mbar). The desired pressure was maintained by continuously taking off a corresponding quantity of gas downstream of the blower.

The catalyst precursor was calcined by heating it in the tray oven in a gas atmosphere of 2.5% by volume oxygen in nitrogen to 350° C., with a temperature ramp of 2° C./min, and was left under these conditions for 25 minutes. Fresh gas mixture was supplied continuously. Thereafter the gas atmosphere was replaced by a nitrogen/steam atmosphere (1:1) and the catalyst precursor was heated to 450° C. at 4° C./min and left for 4 hours. Finally, it was cooled under a nitrogen atmosphere.

The calcining conditions set in the comparative example (Example 2) were optimized in preliminary experiments in respect of the preparation of a catalyst with an average vanadium oxidation state as close as possible to that of the catalyst from the inventive example, Example 1. The differences in the individual parameters are therefore due to the necessary optimization.

After calcination, samples were taken from arbitrarily selected points on the metal trays, and were analyzed for the average oxidation state of the vanadium, for the lateral compressive strength and for the geometric density. The results obtained are set out in Table 4.

TABLE 4

Characterization of the catalyst calcined in the tray oven.

| Catalyst sample (number) | $V_{ox.}$ | LCS [N] | geometric density $d_p$ [g/mL] |
|---|---|---|---|
| 1 | 4.05 | 9 | 1.53 |
| 2 | 4.20 | 14 | 1.68 |
| 3 | 4.05 | 9 | 1.57 |
| 4 | 4.20 | 12 | 1.68 |
| Average: | 4.13 | 11 | 1.62 |

$V_{ox.}$ = average oxidation state of the vanadium
LCS = lateral compressive strength As compared with the characterization data for the catalyst calcined in accordance with the invention, by continuous calcination in a belt calcining means, the catalyst calcined batchwise in a tray oven displays very large ranges of spread. For instance, the average oxidation state of the vanadium in the statistically selected samples varies from 4.05 to 4.20, with the arithmetic average being 4.13. The lateral compressive strength and the geometric density as well exhibit a broad scatter of from 9 to 14 N, with an average of 11 N, and from 1.53 to 1.68 g/mL, with an average of 1.62 g/mL, respectively.

Example 4

Catalytic Test of the Catalyst from Example 3

Using 2.2 L of a statistical mixture of the catalyst from Example 3, calcined batchwise in a tray oven, a catalytic performance test was carried out in the experimental plant described above. The salt bath temperature was set so as to give an n-butane conversion of approximately 85%. The results obtained are reproduced in Table 5.

TABLE 5

Results of the catalytic tests

|  | Catalyst from Example 1 (continuous calcination in a belt calciner) | Catalyst from Example 3 (batchwise calcination in a tray oven) |
|---|---|---|
| Salt bath temperature [° C.] | 395 | 410 |
| Temperature of the hot spots [° C.] | 425 | 434 |
| Pressure drop [MPa] | 0.13 | 0.13 |
| Conversion U [%] | 84.8 | 85.0 |
| Yield A [%] | 57.5 | 56.7 |

A comparison of the results of those for the inventively prepared catalyst of Example 1 shows that owing to the wide range of spread for the comparative catalyst it is necessary to set a salt bath temperature which is higher by 15° C. (410° C. as against 395° C.) in order to bring about the 85% n-butane conversion. Consequently, with the comparative catalyst a hot spot temperature higher by 9° C. is reached. The lower temperature level achieved by the catalyst of the invention is advantageous on a number of grounds. For example, the thermal load on the catalyst is lower, leading to a longer lifetime. The risk of "runaway" of the reaction is likewise reduced owing to the lower temperature level. Moreover, the catalyst operates more selectively, leading to a higher yield of target product for a given conversion. This can also be seen from the experimental data (57.5% yield in the case of the inventively prepared catalyst as against 56.7% yield in the comparative example).

TABLE 3

Characterization of the inventively prepared catalyst.

| Catalyst sample after x t | $V_{ox.}$ | LCS [N] | geometric density $d_p$ [g/mL] | Reject rate after fall test [% by weight] | Abrasion [% by weight] |
|---|---|---|---|---|---|
| 1.47 | 4.16 | 8.7 | 1.51 | 2.0 | 0.8 |
| 1.70 | 4.16 | 10.1 | 1.55 | 3.6 | 0.4 |
| 1.99 | 4.16 | 9.9 | 1.55 | 4.7 | 0.9 |
| 2.19 | 4.14 | 11.2 | 1.55 | 3.5 | 0.7 |
| 2.35 | 4.15 | 8.4 | 1.56 | 3.3 | 0.7 |
| 2.51 | 4.17 | 11.4 | 1.58 | 2.1 | 0.9 |
| 2.67 | 4.17 | 11.3 | 1.58 | 4.0 | n.d. |
| Average: | 4.16 | 10.1 | 1.55 | 3.3 | 0.7 | n.d. = not determined
$V_{ox.}$ = average oxidation state of the vanadium
LCS = lateral compressive strength

We claim:

1. A process for preparing a vanadium, phosphorus, and oxygen containing catalyst suitable for heterogeneously catalyzed gas-phase oxidation of a hydrocarbon having at least four carbon atoms to maleic anhydride, in which a corresponding vanadium, phosphorus, and oxygen containing catalyst precursor containing particles having an averaged diameter of at least 2 mm is converted into a catalytically active form by calcining, which comprises passing a stream of the catalyst precursor for calcining at substantially constant speed through at least one calcining zone n of length $1_n$ on a conveyor belt, the fluctuation in the gas temperature from a setpoint value over time at each point in the region of the stream of the catalyst precursor after half the length of the calcining zone, $1_n/2$, being in each case $\leq 5°$ C. and the local difference in gas temperature between any two points in the region of the stream of the catalyst precursor after half the length of the calcining zone, $1_n/2$, being in each case $\leq 5°$ C.

2. A process as claimed in claim 1, wherein a gas-permeable conveyor belt is used and a gas stream is passed through the stream of the catalyst precursor perpendicularly to its direction of advance in the calcining zone n.

3. A process as claimed in claim 1, wherein a gas circulation system is set up in the calcining zone n, the volume of gas circulating in the calcining zone n per unit time being greater than the volume of gas supplied to the calcining zone n per unit time.

4. A process as claimed in claim 3, wherein a fan is used to generate the gas circulation system.

5. A process as claimed in claim 1, wherein the fluctuation in the gas temperature from said setpoint value over time at each point in the region of the stream of the catalyst precursor after half the length of the calcining zone, $1_n/2$, is in each case $\leq 2°$ C.

6. A process as claimed in claim 1, wherein the local difference in gas temperature between any two points in the region of the stream of the catalyst precursor after half the length of the calcining zone, $1_n/2$, is $\leq 3°$ C.

7. A process as claimed in claim 1, wherein the stream of the catalyst precursor for calcining is passed through at least two calcining zones and the temperatures of the individual calcining zones can be regulated independently of one another.

8. A process as claimed in claim 7, wherein a temperature increase between successive calcining zones is up to 225° C.

9. A process as claimed in claim 7, wherein the gas supplied to a successive calcining zone comprises nitrogen and steam, or nitrogen.

10. A process as claimed in claim 9, wherein the gas supplied tote successive calcining zone comprises steam.

11. A process as claimed in claim 1, wherein a catalyst precursor is used which has substantially a hollow cylindrical structure.

12. A process as claimed in claim 1, wherein the catalyst precursor
    (a) is heated to a temperature of from 200 to 350° C. in at least one calcining zone in an oxidizing atmosphere having an oxygen content of from 2 to 21% by volume and is left under these conditions until the desired average oxidation state of the vanadium is reached; and
    (b) is heated to a temperature of from 300 to 500° C. in at least one further calcining zone in a nonoxidizing atmosphere having an oxygen content of $\leq 0.5\%$ by volume and a hydrogen oxide content of from 20 to 75% by volume and is left under these conditions for $\leq 0.5$ hour.

13. A process as claimed in claim 1, wherein a catalyst is prepared which has a phosphorus/vanadium atomic ratio of from 0.9 to 1.5, an average oxidation state of the vanadium of from +3.9 to +4.4, a BET surface area of from 10 to 50 m²/g, a pore volume of from 0.1 to 0.5 mug, and a bulk density of from 0.5 to 1.5 kg/l.

14. A process as claimed in claim 1, wherein the vanadium, phosphorus, and oxygen containing catalyst comprises a phosphate.

15. A process as claimed in claim 14, wherein the vanadium, phosphorus, and oxygen containing catalyst comprises vanadyl pyrophosphate.

* * * * *